(12) United States Patent
Shibata et al.

(10) Patent No.: US 9,732,314 B2
(45) Date of Patent: Aug. 15, 2017

(54) APPARATUS FOR CULTURING CELLS

(71) Applicant: Panasonic Corporation, Osaka (JP)

(72) Inventors: Norihiro Shibata, Osaka (JP); Toshiaki Yamauchi, Kyoto (JP); Takeshi Ando, Kyoto (JP)

(73) Assignee: Panasonic Corporation, Osaka (JP)

(*) Notice: Subject to any disclaimer, the term of this patent is extended or adjusted under 35 U.S.C. 154(b) by 0 days.

(21) Appl. No.: 15/075,109

(22) Filed: Mar. 19, 2016

(65) Prior Publication Data
US 2016/0298069 A1    Oct. 13, 2016

(30) Foreign Application Priority Data
Apr. 10, 2015  (JP) .................. 2015-081100

(51) Int. Cl.
| C12M 1/00 | (2006.01) |
| C12M 1/26 | (2006.01) |
| C12M 1/12 | (2006.01) |
| C12M 1/36 | (2006.01) |
| C12M 3/00 | (2006.01) |
| C12M 1/22 | (2006.01) |

(52) U.S. Cl.
CPC ............ *C12M 23/34* (2013.01); *C12M 21/08* (2013.01); *C12M 23/06* (2013.01); *C12M 23/10* (2013.01); *C12M 23/48* (2013.01); *C12M 23/50* (2013.01); *C12M 29/00* (2013.01); *C12M 33/04* (2013.01); *C12M 37/00* (2013.01); *C12M 41/48* (2013.01)

(58) Field of Classification Search
CPC ...... C12M 21/08; C12M 23/10; C12M 23/34; C12M 23/48; C12M 23/50; C12M 29/00; C12M 33/04; C12M 37/00; C12M 41/48
See application file for complete search history.

(56) References Cited

U.S. PATENT DOCUMENTS

2005/0260742 A1* 11/2005 Watanabe .............. C12M 23/50
                                                   435/287.3
2011/0159578 A1*  6/2011 Godsey .............. G01N 35/1002
                                                   435/287.1

FOREIGN PATENT DOCUMENTS

| JP | 2005-287465 | 10/2005 |
| JP | 2009-291104 | 12/2009 |

OTHER PUBLICATIONS

The Extended European Search Report dated Aug. 23, 2016 for the related European Patent Application No. 16159335.5.

* cited by examiner

*Primary Examiner* — Nathan Bowers
*Assistant Examiner* — Lydia Edwards
(74) *Attorney, Agent, or Firm* — Panasonic IP Management; Kerry S. Culpepper

(57) ABSTRACT

An apparatus for culturing cells of the present disclosure includes: a cabinet that has a main surface and a side surface, the main surface having a window; a main surface aspiration port disposed at the main surface of the cabinet; and a side surface aspiration port disposed at the side surface of the cabinet. In the cross section of the cabinet taken along the horizontal direction, a first vessel supplying part for supplying a first vessel is disposed at a midportion of the cabinet, and a second vessel supplying part for supplying a second vessel is disposed at an inner peripheral portion of the cabinet. The first vessel supplying part has a first lid capable of entirely covering the first vessel supplying part. The first vessel has no lid. The second vessel supplying part has no lid. The second vessel has a second lid.

8 Claims, 2 Drawing Sheets

APPARATUS FOR CULTURING CELLS

This application claims the benefit of Japanese Application No. 2015-081100, filed on Apr. 10, 2014, the disclosure of which Application is incorporated by reference herein.

BACKGROUND

1. Technical Field

The present disclosure relates to an apparatus for culturing cells.

2. Description of the Related Art

Generally, cells are cultured with a liquid culture medium such as a culture solution and a solid culture medium such as agar, each containing a large amount of nutrients (hereinafter referred to as a culture medium). Here, use of a culture medium for long hours disadvantageously influences growth of cells. Accordingly, the culture medium must be replaced periodically. The current manually-performed culture medium replacement is now becoming difficult to address a large number of culture vessels. Therefore, there is demand for an apparatus for culturing cells which can automate culture medium replacement. Conventionally, what is disclosed is a layout structure for automating cell cultivation in which devices are disposed along the installation plane being parallel to a housing (for example, see Unexamined Japanese Patent Publication No. 2009-291104).

The conventional layout of the apparatus for culturing cells does not fully take into consideration of the influence of contamination attributed to disturbed airflow caused by an opened window of the apparatus for supplying consumables required for cell cultivation, the influence on the operating time of the culturing apparatus and the like.

SUMMARY

Accordingly, an object of the present disclosure is to provide layout which improves supply work efficiency and prevents contamination by airflow occurring when a window is opened for supplying consumables and the like, in consideration of also the operating time of the culturing apparatus.

In order to achieve the object stated above, an apparatus for culturing cells of the present disclosure includes: a cabinet that has a main surface and a side surface, the main surface having a window; a main surface aspiration port disposed at the main surface of the cabinet; and a side surface aspiration port disposed at the side surface of the cabinet. In a cross section of the cabinet taken along a horizontal direction, a first vessel supplying part for supplying a first vessel is disposed at a midportion of the cabinet, and a second vessel supplying part for supplying a second vessel is disposed at an inner peripheral portion of the cabinet. The first vessel supplying part has a first lid capable of entirely covering the first vessel supplying part. The first vessel has no lid. The second vessel supplying part has no lid. The second vessel has a second lid.

As described above, with the apparatus for culturing cells of the present disclosure, contamination is prevented by virtue of the consumable having a lid being disposed at each of the right and left parts in the cabinet, and a reduction in work hours is realized by virtue of the consumables having no lid being disposed at the midportion.

DETAILED DESCRIPTION OF THE PREFERRED EMBODIMENT

Next, with reference to the drawings, a description will be given of an exemplary embodiment of an apparatus for culturing cells of the present disclosure. Note that, the following exemplary embodiment is merely an exemplary apparatus for culturing cells of the present disclosure. Accordingly, the scope of the present disclosure is limited by the language of the claims with reference to the following exemplary embodiment, and not limited solely to the following exemplary embodiment. Hence, among the constituent elements described in the following exemplary embodiment, those not described in an independent claim representing the most generic concept of the present disclosure are not being essential for achieving the object of the present disclosure, but are for structuring a more preferable mode.

In the following, with reference to the drawings, a description will be given of the exemplary embodiment of the present disclosure. Further, for the sake of clarity, the drawings schematically show mainly the constituent elements.

Exemplary Embodiment

Figure 1:
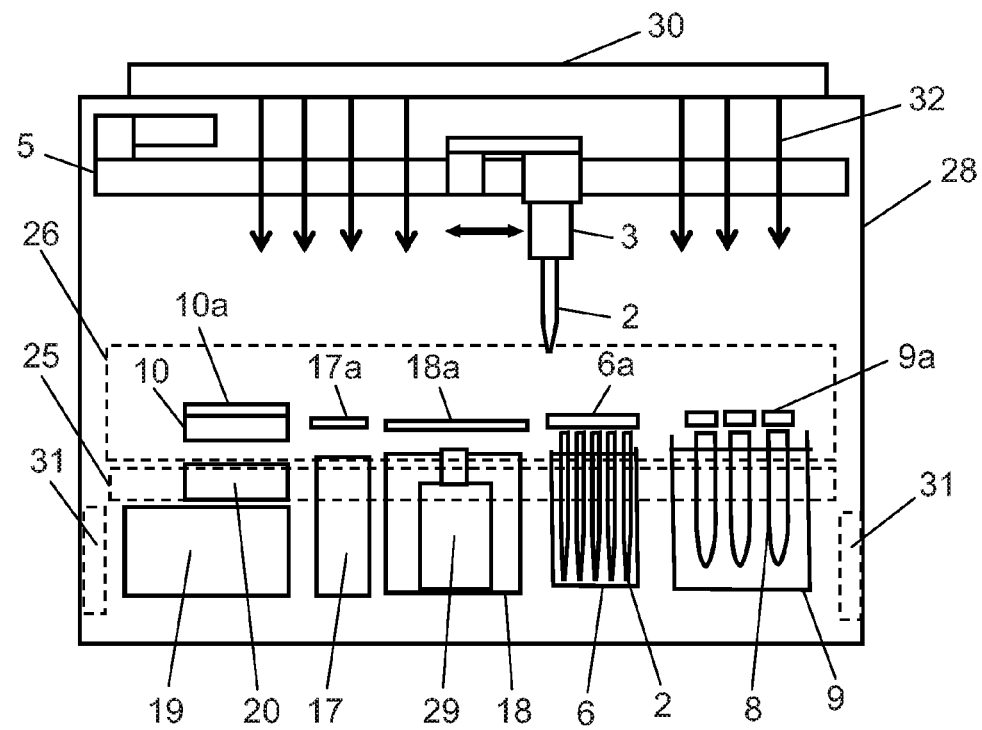
FIG. 1 is a front view showing the overview of an apparatus for culturing cells according to an exemplary embodiment of the present disclosure.
Figure 2:
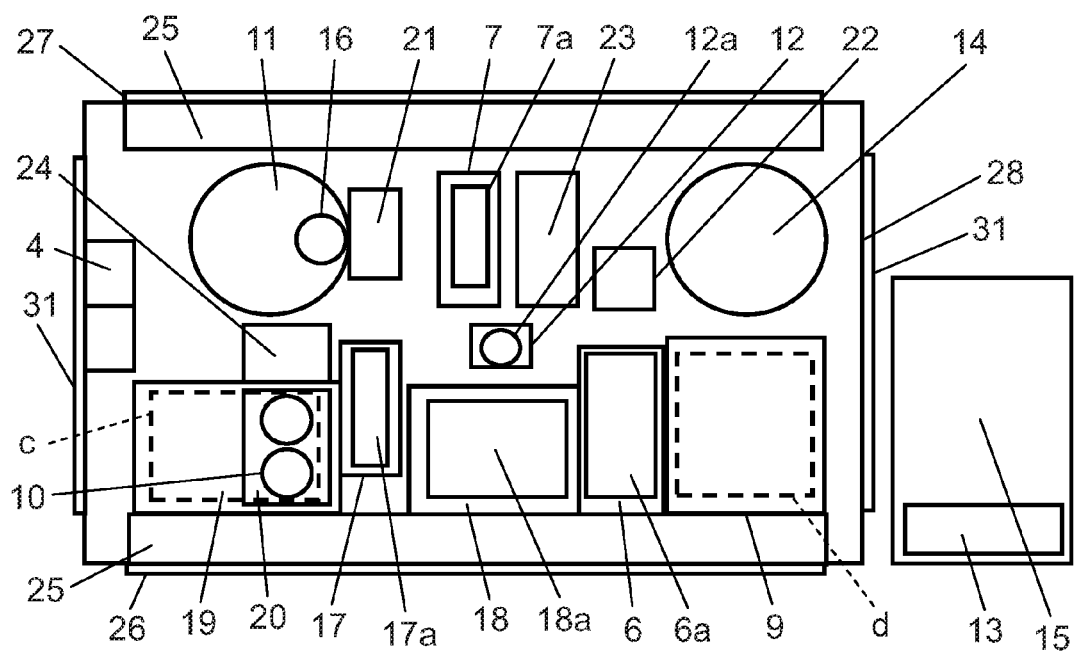
FIG. 2 is a top view showing the overview of the apparatus for culturing cells according to the exemplary embodiment of the present disclosure.

FIGS. 1 and 2 are schematic diagrams of apparatus for culturing cells 1 according to an exemplary embodiment of the present disclosure. FIG. 1 is a schematic diagram of the constituent elements inside apparatus for culturing cells 1 as seen from the main side. FIG. 2 is a schematic diagram of the constituent elements inside apparatus for culturing cells 1 as seen from above.

Apparatus for culturing cells 1 is an apparatus for culturing cells in a managed space, and includes cabinet 28, vessel supplying part 9, vessel supplying part 20, vessel supplying part 6, and vessel supplying part 18. Apparatus for culturing cells 1 according to the exemplary embodiment further includes vessel holder 3 and robot 5. Apparatus for culturing cells 1 is characterized in that vessel supplying part 9 and vessel supplying part 20 are respectively disposed on the opposite sides in cabinet 28, and vessel supplying part 6 and vessel supplying part 18 are disposed between vessel supplying part 9 and vessel supplying part 20.

Cabinet 28 is a housing whose overall shape is an approximate rectangular parallelepiped and which forms a space in which flow of air is blocked. Cabinet 28 includes a window being an opening at its main surface (front surface). Further, the window is provided with cover 26 capable of opening and closing. In the present exemplary embodiment, cover 26 is a sliding cover. Further, in cabinet 28, main surface aspiration port 25 is disposed below cover 26 (window), and side surface aspiration ports 31 are disposed at the bottom of the opposite side surfaces of cabinet 28. Note that, being disposed at the bottom of the side surfaces means the state of being disposed on the lower side than the center of the side surfaces. More specifically, it means the state of the lower sides of side surface aspiration ports 31 being in contact with the bottom surface of cabinet 28. By disposing side surface aspiration ports 31 in this manner, the inside of cabinet 28 can be kept at a higher level of cleanliness.

The window provided at the main surface has a shape of a laterally elongated rectangle extending across almost the entire main surface in the width direction.

Vessel supplying part 9 is disposed inside cabinet 28 for supplying vessel 8 having a lid. In the present exemplary embodiment, vessel 8 is a tube sealed by lid 9a.

Vessel supplying part 20 is disposed inside cabinet 28 for supplying vessel 10 having a lid. In the present exemplary embodiment, vessel 10 is a culture vessel for culturing cells, and is a dish (petri dish) or a plate sealed by lid 10a.

Vessel supplying part 6 is disposed inside cabinet 28 for supplying vessel 2 having no lid. In the present exemplary embodiment, vessel 2 is a pipet chip in the open state with no lid. Note that, in the present specification, the claims and the drawings, the term vessel includes an instrument which temporarily holds liquid, such as a pipet chip.

Vessel supplying part 18 is disposed inside cabinet 28 for supplying vessel 29 having no lid. In the present exemplary embodiment, vessel 29 is a bottle for storing a reagent, in the open state with no lid. Further, vessel supplying part 18 functions as a refrigerator for maintaining the reagent at a prescribed temperature. By storing the content of vessel 29 at low temperatures, the content such as a reagent can be prevented from being decomposed.

Vessel holder 3 is a mechanism capable of holding vessel 2 for supplying a culture medium or a chemical solution to vessel 10.

Robot 5 can shift vessel 2 held by vessel holder 3 inside cabinet 28.

Here, vessel 2, vessel 8, vessel 29, and vessel 10 are consumables.

The tube being vessel 8 is a consumable for temporarily storing a reagent or for performing an operation on cells.

The bottle for storing a reagent being vessel 29 is a consumable for storing the reagent temporarily stored in vessel 8 in a greater amount. In order to maintain the quality of the reagent, vessel supplying part 18 has the function of keeping vessel 29 at low temperatures.

Note that, vessel supplying part 20 is a stocker in which restriction pins are set conforming to the outer shape of each vessel for storing reserve vessel 10.

Apparatus for culturing cells 1 further includes heater 17 for heating the reagent to temperatures suitable for cell cultivation when the reagent is supplied to cells. Further, in order to prevent contamination, heater 17 is provided with heater-use lid 17a provided so as to be capable of opening and closing. Note that, vessel supplying part 18 also is provided with vessel supplying part-use lid 18a and vessel supplying part 6 also is provided with vessel supplying part-use lid 6a for preventing contamination. The reagent stored at low temperatures at vessel supplying part 18 is not suitable for cell culture because of being cold. Accordingly, heater 17 has a function of heating the reagent to temperatures suitable for cell culture. For example, when the cells desired to culture are human iPS cells, heater 17 heats the reagent to temperatures from 35° C. to 38° C. inclusive. Note that, the reagent is stored in the refrigerator at 10° C. or lower.

At the ceiling of cabinet 28, supply port 30 for supplying clean air 32 as downward airflow (downflow) from the ceiling is provided.

Additionally, there is incubator 19 for culturing cells in vessel 10.

Further, there is syringe pump 4 (see FIG. 2) connected to vessel 2 held by vessel holder 3 and discharges/draws in liquid to and from vessel 2.

Still further, there is vessel lid opener 23 shown in FIG. 2 which opens and closes lid 9a of vessel 8 by gripping a lid by an air chuck shown in FIG. 1 and rotating the lid by a servomotor, turntable 11 for holding vessel 10, vessel shaker 16 which grips and shakes vessel 10, and vessel lid opener/closer 21 which grips the lid of vessel 10 by an air chuck, shifts in the lateral direction by a rotary cylinder, and opens and closes the lid. Further, there is centrifuge 14 for centrifuging cells in the reagent.

Still further, there is waste water tank 12 for discarding the used reagent, waste water tank-use lid 12a being the lid of waste water tank 12, dustbin 7 for discarding consumables such as used vessel 10 and the like, and dustbin-use lid 7a being the lid of dustbin 7.

Still further, there is provided output part 24 which raises and lowers vessel 10 using a servomotor for automatically putting in and taking out vessel 10 to and from incubator 19.

Note that, there is tool 22 which has two types of grippers conforming to the shape of a gripped object for manipulation in each operation.

Here, the reagent is an iPS cell-use culture medium, a dissociation agent such as PBS, trypsin or the like. Note that, the culture medium is liquid for promoting the growth of cells attached onto vessel 10.

Here, in the case where cell cultivation is carried out using apparatus for culturing cells 1, it is necessary to supply vessel 2, vessel 8, vessel 10, and vessel 29 being consumables into cabinet 28. To this end, the window capable of being opened and closed by cover 26 disposed at the main surface of cabinet 28 is provided. By opening the window, the inside and the outside of cabinet 28 are allowed to communicate with each other, and the consumables are supplied. Further, in order to carry out maintenance of the rear surface portion which cannot be reached from the window by hands, a window covered by cover 27 so as to be capable of opening and closing is provided at the rear surface of cabinet 28. The covers are provided at a height where supply to the consumable supplying parts is facilitated. For example, the lower edge of the covers is at a height of 114.5 cm from the floor surface, and the covers have a width of 153.2 cm, and a height of 20 cm.

Further, main surface aspiration port 25 is provided below cover 26 (the window) of cabinet 28. Main surface aspiration port 25 is provided with a cover having a hole for adjusting the opening proportion, so as to prevent the inside air and the outside air from being replaced by each other. Main surface aspiration port 25 maintains cleanliness of the inside of cabinet 28 even in the state where cover 26 is opened, by simultaneously aspirating the air inside the cabinet 28 and the outside air.

Still further, in order to maintain the cleanliness inside cabinet 28, clean air 32 is supplied from supply port 30 at the upper portion, to create downward airflow. At this time, in order to prevent dust from being raised by whirling airflow generated at the bottom of cabinet 28, side surface aspiration ports 31 are provided for aspirating air from the bottom side surfaces of cabinet 28. Thus, downward airflow of clean air 32 is maintained smoothly. At this time, the opening proportion of main surface aspiration port 25 is 40% for example, and the opening proportion of side surface aspiration ports 31 is 1% for example.

Main surface aspiration port 25 is provided in the entire width direction of the window closed by cover 26.

In order to secure the height at which consumables can be easily supplied, the consumable supplying parts are at positions, for example, higher than main surface aspiration port 25 by 30 mm, and side surface aspiration ports 31 are at positions, for example, lower than main surface aspiration port 25 by 80 mm, so as to aspirate air existing at portions lower than main surface aspiration port 25.

Since the aspiration ports are provided in this manner, airflow entering inside cabinet 28 is prone to occur at left and right portions c, d (see FIG. 2) relative to the window (cover 26) because of left and right portions c, d being positioned near the aspiration ports of side surface aspiration ports 31. Such airflow creates an environment where contamination by dust contained in the outside air is particularly prone to occur. Addressing the environment, vessel supplying part 9 and vessel supplying part 20 are disposed near left and right portions c, d. This is because vessel 8 for temporarily storing a reagent necessary at the preparation stage of the culture work or for manipulating cells, and vessel 10 used at the final stage of taking the cultured cells to the outside of the apparatus are respectively provided with individual lid 9a and lid 10a for vessel 10. The lids prevent entry of dust into the consumables. That is, it is suitable to dispose vessel 8 and vessel 10 being consumables with lids respectively at left and right portions c, d, which are the side surfaces of cabinet 28 where risk of contamination is the highest.

On the other hand, vessel 2 and vessel 29 supplied to vessel supplying part 18, heater 17, and vessel supplying part 6 are used in automated culture at high frequency. Therefore, provision of individual lids to the consumables increases the work hours. Accordingly, vessel 2 and vessel 29 are not provided with lids, and disposed at positions being spaced apart from portions c, d (side surface aspiration ports 31). In this case, in order to further reduce the risk of contamination, lids respectively covering the supplying parts (vessel supplying part 18, heater 17, vessel supplying part 6) for supplying the consumables with no individual lids (vessel 2 and vessel 29) are provided.

Further, from the viewpoint of preventing contamination, it is necessary to reduce the opening area of the window. On the other hand, it is also necessary to secure workability of supplying the consumables. Accordingly, it is more preferable to reduce the opening area of the window as much as possible, and to dispose the supply ports of the supplying parts of the consumables (vessel supplying part 6, vessel supplying part 9, vessel supplying part 20, and vessel supplying part 18) near (in opposition to) the window (cover 26), and in line.

As described above, the disposition of the consumable supplying parts for reducing the risk of contamination and improving the work efficiency is summarized as follows. That is, out of the vessel supplying parts which supply vessels being consumables, vessel supplying part 9 and vessel supplying part 20 for supplying consumables with individual lids are respectively disposed at the positions nearest to left and right portions c, d being the opposite sides of cabinet 28. Vessel supplying part 18, heater 17, and vessel supplying part 6 for supplying consumables without individual lids are disposed at the midportion of cabinet 28, that is, at the position between vessel supplying part 9 and vessel supplying part 20.

Here, intervals between the disposed positions are exemplarily shown. At this time, vessel supplying part 9 is spaced apart from main surface aspiration port 25 by 5 cm to 7 cm, and from side surface aspiration port 31 by 124 cm to 126 cm. Further, vessel supplying part 20 is spaced apart from main surface aspiration port 25 by 2 cm to 4 cm, and from side surface aspiration port 31 by 34 cm to 36 cm. Vessel supplying part 18 is spaced apart from main surface aspiration port 25 by 1 cm to 3 cm, and from side surface aspiration port 31 by 74 cm to 76 cm. Still further, heater 17 is spaced apart from main surface aspiration port 25 by 13 cm to 15 cm, and from side surface aspiration port 31 by 59 cm to 61 cm. Still further, vessel supplying part 6 is spaced apart from main surface aspiration port 25 by 6 cm to 8 cm, and from side surface aspiration port 31 by 119 cm to 121 cm.

Here, preferably turntable 11 is disposed at the end near vessel supplying part 20. Further, in order to reduce the time during which cells are outside the incubator and to reduce the shift distance in the state where turntable 11 is carrying cells, turntable 11 is disposed at the side of output part 24 of incubator 19.

Note that, in the case where the consumables are supplied, when a consumable desired to be supplied is specified by operation part 13, a consumable supply instruction is issued from controller 15. When controller 15 determines that operations of the apparatuses are stopped and the state where the supply is possible is entered, a safety lock of elongated cover 26 disposed at the front surface of cabinet 28 is released, and opening and closing of the cover by the user is allowed. Here, the user lifts the cover and sets the consumable at a prescribed position.

In the foregoing, a description has been given of the layout of the structures. Note that, front, rear, right and left in the above-described layout may be changed as appropriate.

Subsequently, with reference to the flowchart of FIG. 3 and FIGS. 1 and 2, a description will be given of a method for cultivating cells using apparatus for culturing cells 1, particularly focusing on the operation of replacing a culture medium.

Figure 3:
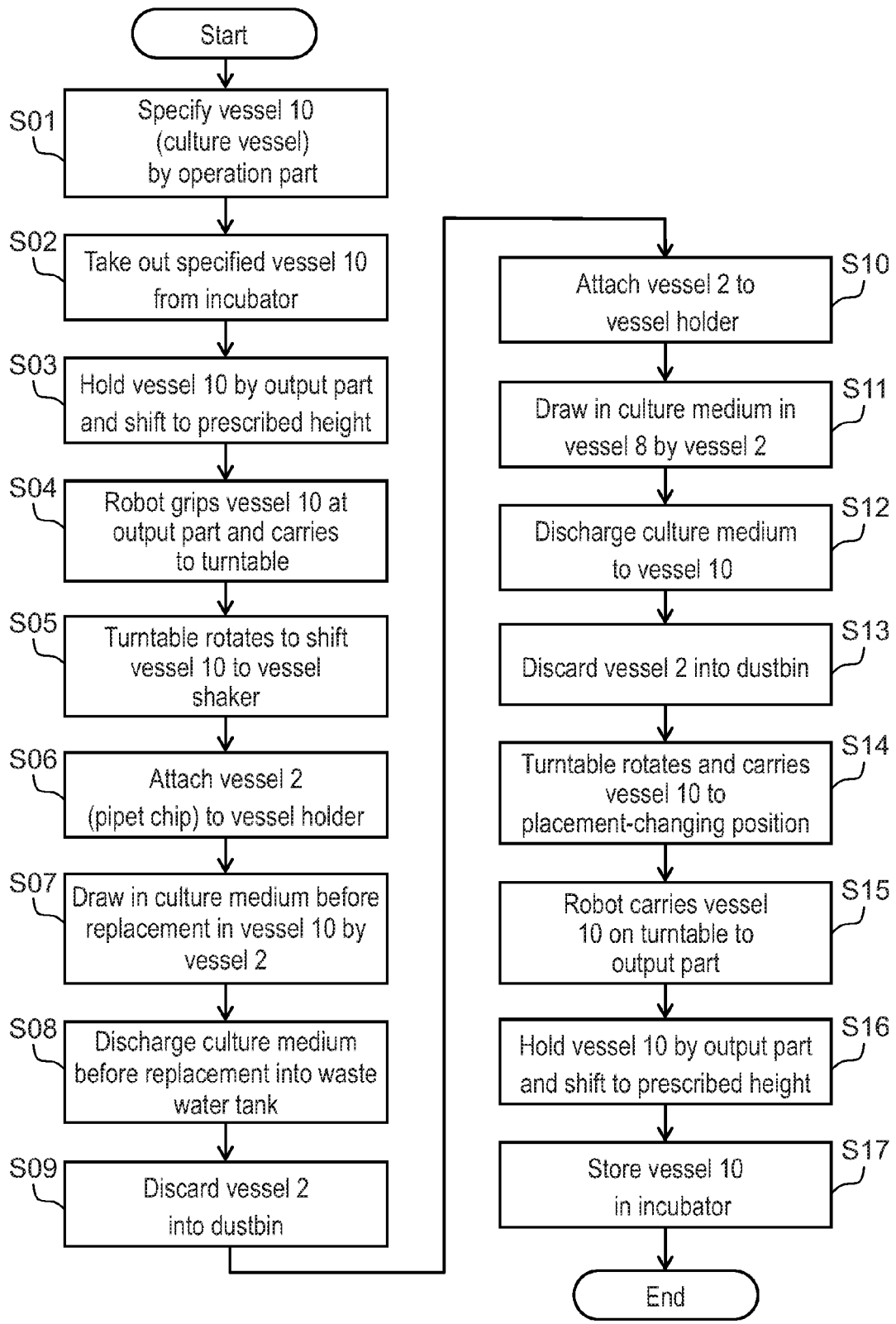
FIG. 3 is a flowchart of culture medium replacement according to the exemplary embodiment.

In Step S01 of FIG. 3, when vessel 10 (a culture vessel) with which culture medium replacement is to be carried out is specified by operation part 13, a culture medium replacement instruction is issued from controller 15. Next, in Step S02, the specified vessel 10 is taken out from incubator 19. In Step S03, output part 24 is caused to hold vessel 10 and shift to a prescribed height. Thereafter, in Step S04, robot 5 grips vessel 10 at output part 24, and carries to turntable 11. In Step S05, turntable 11 rotates to shift vessel 10 to vessel shaker 16.

Subsequently, in Step S06, vessel holder 3 is attached to robot 5, and shifted to a point above vessel supplying part 6. Then, vessel supplying part-use lid 6a is opened, and first vessel 2 (a pipet chip) stored in vessel supplying part 6 is inserted into vessel holder 3 thereby attached.

Subsequently, in Step S07, robot 5 shifts vessel holder 3 to a point above vessel shaker 16. Then, in the state where lid 10a is displaced by vessel lid opener/closer 21 in the horizontal direction, a culture medium before replacement in vessel 10 is drawn in by first vessel 2 (the pipet chip). Thereafter, lid 10a is returned to the initial position.

Subsequently, in Step S08, robot 5 shifts vessel holder 3 to a point above waste water tank 12. Then, waste water tank-use lid 12a is opened, and the culture medium before replacement drawn in by first vessel 2 is discharged to waste water tank 12 thereby discarded. Thereafter, waste water tank-use lid 12a is closed.

Subsequently, in Step S09, robot 5 shifts vessel holder 3 to a point above dustbin 7. Then, dustbin-use lid 7a is opened, and the used first vessel 2 is discarded into dustbin 7. Thereafter, dustbin-use lid 7a is closed.

Subsequently, in Step S10, second vessel 2 is held by vessel holder 3 by the same procedure as Step S06.

Subsequently, in Step S11, robot 5 shifts vessel holder 3 to a point above heater 17. Then, heater-use lid 17a is opened, and a culture medium in vessel 8 (a tube) is drawn in by second vessel 2. Thereafter, heater-use lid 17a is closed. Vessel 8 storing the culture medium in heater 17 at this time has been supplied by the user to vessel supplying part 9, thereafter gripped by robot 5 where tool 22 has been replace for use with vessel 8, and shifted and supplied to heater 17. Note that, the culture medium (the reagent) in vessel 8 is supplied before Step S11 from vessel 29 stored in vessel supplying part 18.

Subsequently, in Step S12, robot 5 shifts vessel holder 3 to a point above vessel shaker 16. Then, in the state where lid 10a is shifted in the horizontal direction by vessel lid opener/closer 21, the culture medium is discharged from second vessel 2 into vessel 10. Thereafter, lid 10a of vessel 10 is returned to the initial position. Then, vessel 10 is shaken by vessel shaker 16, whereby cells in vessel 10 are evenly immersed in the culture medium.

Subsequently, in Step S13, robot 5 shifts vessel holder 3 to a point above dustbin 7. Then, dustbin-use lid 7a is opened, and the used second vessel 2 is discarded into dustbin 7. Thereafter, dustbin-use lid 7a is closed.

Subsequently, in Step S14, turntable 11 is rotated, and vessel 10 is shifted to a placement-changing position.

Subsequently, in Step S15, robot 5 carries vessel 10 to output part 24.

Subsequently, in Step S16, output part 24 shifts to a prescribed height, thereby shifting vessel 10 to incubator 19.

Subsequently, in Step S17, vessel 10 is stored in a prescribed position in incubator 19.

In the foregoing, the operations have been described.

Here, the description has been given of an exemplary case where vessel 10 with which cell cultivation is carried out using a culture medium is stored in incubator 19. Instead, for example, vessel 10 may be stored in other storage such as vessel supplying part 20 as necessary.

Note that, after Step S07, it is desired to take a picture of the inside of vessel 10 with a camera to observe at any timing at least before Step S12. In the case where observation is performed at such timing, the amount of the culture medium before and after replacement can be adjusted in accordance with the observation result. At dissociation of cells in the case where subculture is performed, by observing before and after that step, the type or amount of a dissociation solution can be adjusted in accordance with the observation result. Thus, more accurate cell cultivation can be carried out.

Note that, the flow shown in FIG. 3 is controlled by controller 15 shown in FIG. 2. The control by controller 15 is exerted in accordance with a preset condition, or a condition input from operation part 13 such as a touchscreen.

Note that, in order to prevent the drawn in culture medium before replacement from dripping and attaching to other apparatus and causing contamination, the shift distance of robot 5 is reduced to a minimum. That is, waste water tank 12 is disposed nearest to vessel shaker 16.

Similarly, vessel supplying part 18, heater 17, and waste water tank 12 which are used frequently in culture work are preferably disposed near vessel shaker 16, such that the shift distance of robot 5 becomes a minimum. For example, the distance from the center of vessel shaker 16 to the center of waste water tank 12 is 52 cm; the distance from the center of vessel shaker 16 to the end of vessel supplying part 18 is 34 cm; and the distance from the center of vessel shaker 16 to the end of heater 17 is 25 cm.

Vessel supplying part 6, vessel supplying part 18, and heater 17 are also preferably disposed in accordance with the order of attaching vessel 2 to vessel holder 3, drawing in a reagent from vessel 29 in vessel supplying part 18, and discharging the reagent to heater 17. When this disposition is changed, vessel 2 having drawn in a reagent passes above vessel supplying part 18, vessel supplying part 6 and the like. This may cause contamination by dripping. For example, disposition dimension of the apparatuses is as follows. The distance between vessel supplying part 20 and heater 17 is 1.5 cm; the distance between heater 17 and vessel supplying part 18 is 0.5 cm; the distance between vessel supplying part 18 and vessel supplying part 6 is 0.8 cm; and the distance between vessel supplying part 6 and vessel supplying part 9 is 1.45 cm.

Note that, vessel 8 is a tube for temporarily storing a reagent or cells. Vessel 10 is a petri dish for culturing the cells. Vessel 2 is a pipet chip for drawing in or discharging the reagent. Vessel 29 is a reagent storage bottle for storing the reagent.

Note that, in order to prevent vibrations of centrifuge 14 from transmitting to cells being cultured, centrifuge 14 and incubator 19 are spaced apart from each other by a maximum distance. In the present exemplary embodiment, by diagonally disposing centrifuge 14 and incubator 19 in a plan view, the distance is maximized as compared to other structure.

Note that, the present disclosure is not limited to the exemplary embodiment described above. For example, other exemplary embodiment realized by any combination of the constituent elements described above or omission of some constituent elements may be regarded as an exemplary embodiment of the present disclosure. Further, the present disclosure also includes a variation obtained by applying modifications contemplated by a person skilled in the art to the above-described exemplary embodiment within the spirit of the present disclosure, that is, within the meaning of the language of the claims.

For example, an apparatus for culturing cells of the present disclosure includes: cabinet 28 that has a main surface and a side surface, the main surface having a window; main surface aspiration port 25 disposed at the main surface of cabinet 28; and side surface aspiration port 31 disposed at the side surface of cabinet 28. In a cross section of cabinet 28 taken along the horizontal direction (see FIG. 2), vessel supplying part 6 for supplying vessel 2 and vessel supplying part 18 for supplying vessel 29 are disposed at a midportion of cabinet 28. Vessel supplying part 9 for supplying vessel 8 and vessel supplying part 20 for supplying vessel 10 are disposed at the inner peripheral portion (the region near the side surfaces than the midportion) of the cabinet 28.

Vessel supplying part 6 has lid 6a capable of covering the entire vessel supplying part 6, and vessel 2 has no lid. Similarly, vessel supplying part 18 has lid 18a capable of covering the entire vessel supplying part 18, and vessel 29 has no lid. On the other hand, vessel supplying part 9 has no lid, and vessel 8 has lid 9a. Similarly, vessel supplying part 20 has no lid, and vessel 10 has lid 10a.

Vessel supplying part 6 may supply one or more vessel 6. Vessel supplying part 9 may supply one or more vessel 8. Vessel supplying part 18 may supply one or more vessel 29. Vessel supplying part 20 may supply one or more vessel 10.

In the cross section of cabinet 28 taken along the horizontal direction (see FIG. 2), vessel supplying part 6 and vessel supplying part 18 are disposed nearer to the center of cabinet 28 than vessel supplying part 9 and vessel supplying part 20 are.

The apparatus for culturing cells of the present disclosure is useful in cell culture in regenerative medicine and drug discovery fields.

What is claimed is:

1. An apparatus for culturing cells comprising:
a cabinet that has a main surface having a window, and a side surface;
a main surface aspiration port disposed at the main surface of the cabinet and provided below the window; and
a side surface aspiration port disposed at the side surface of the cabinet,
wherein in a cross section of the cabinet taken along a horizontal direction,
a first vessel supplying part for supplying a first vessel is disposed at a midportion of the cabinet, and
a second vessel supplying part for supplying a second vessel is disposed at an inner peripheral portion of the cabinet,
the first vessel supplying part has a first lid capable of entirely covering the first vessel supplying part,
the first vessel has no lid,
the second vessel supplying part has no lid, and
the second vessel has a second lid.

2. The apparatus for culturing cells according to claim 1, wherein
the first vessel supplying part supplies at least one vessel including the first vessel, and
the second vessel supplying part supplies at least one vessel including the second vessel.

3. The apparatus for culturing cells according to claim 1, wherein, in the cross section of the cabinet taken along the horizontal direction, the first vessel supplying part is positioned nearer to a center of a cabinet than the second vessel supplying part is.

4. The apparatus for culturing cells according to claim 1, wherein
the first vessel is one of a pipet chip for drawing in and discharging a reagent and a reagent storage bottle for storing a reagent, and
the second vessel is one of a tube for storing a reagent or cells and a petri dish for culturing cells.

5. The apparatus for culturing cells according to claim 1, wherein the first vessel is more frequently used in cell cultivation and less influenced by contamination with dust when outside air is aspirated than the second vessel.

6. The apparatus for culturing cells according to claim 1, further comprising a vessel lid opener including an air chuck configured to open and close the second lid.

7. The apparatus for culturing cells according to claim 1, wherein the window is provided with a cover configured to open or close to provide interior access to the cabinet.

8. The apparatus for culturing cells according to claim 1, wherein the first and second vessel supplying parts are disposed higher than the main surface aspiration port, and the side surface aspiration port is disposed lower than the main surface aspiration port.

* * * * *